(12) United States Patent
Kiehne (10) Patent No.: US 8,313,459 B2
(45) Date of Patent: Nov. 20, 2012

(54) MEDICAL IMPLEMENT INSERTION DEVICE

(75) Inventor: Bruce Leigh Kiehne, Queensland (AU)

(73) Assignee: Chelsea Brands Pty Ltd, Slacks Creek (AU)

( * ) Notice: Subject to any disclaimer, the term of this patent is extended or adjusted under 35 U.S.C. 154(b) by 83 days.

(21) Appl. No.: 12/939,287

(22) Filed: Nov. 4, 2010

(65) Prior Publication Data

US 2012/0041372 A1 Feb. 16, 2012

(30) Foreign Application Priority Data

Aug. 13, 2010 (AU) ................................ 2010903644

(51) Int. Cl.
*A61M 5/00* (2006.01)
*A61M 5/178* (2006.01)
(52) U.S. Cl. ................................... 604/110; 604/164.07
(58) Field of Classification Search ................... 604/110, 604/164.01, 164.06, 164.07, 164.12
See application file for complete search history.

(56) References Cited

U.S. PATENT DOCUMENTS

| | | | |
|---|---|---|---|
| 5,575,777 A | 11/1996 | Cover et al. | |
| 5,599,310 A | 2/1997 | Bogert | |
| 5,797,880 A | 8/1998 | Erskine | |
| 5,817,058 A | 10/1998 | Shaw | |
| 5,989,220 A | 11/1999 | Shaw et al. | |
| 6,287,278 B1 | 9/2001 | Woehr et al. | |
| 7,753,887 B2* | 7/2010 | Botich et al. | 604/164.12 |
| 7,879,010 B2* | 2/2011 | Hunn et al. | 604/164.12 |
| 8,048,031 B2* | 11/2011 | Shaw et al. | 604/164.07 |
| 2004/0122373 A1 | 6/2004 | Botich et al. | |
| 2004/0158207 A1* | 8/2004 | Hunn et al. | 604/164.01 |
| 2005/0015053 A1* | 1/2005 | Parker | 604/164.12 |
| 2005/0075606 A1* | 4/2005 | Botich et al. | 604/110 |
| 2005/0245875 A1* | 11/2005 | Restelli et al. | 604/164.01 |
| 2006/0200080 A1* | 9/2006 | Abulhaj | 604/164.01 |
| 2010/0168674 A1* | 7/2010 | Shaw et al. | 604/164.07 |
| 2011/0125097 A1* | 5/2011 | Shaw et al. | 604/164.12 |

FOREIGN PATENT DOCUMENTS

| | | |
|---|---|---|
| WO | WO 96/20026 | 7/1996 |
| WO | WO 96/27403 | 9/1996 |
| WO | WO 98/13077 | 4/1998 |
| WO | WO 99/24092 | 5/1999 |

OTHER PUBLICATIONS

Office Communication issued in corresponding European Patent Application No. 10188458.3 on Nov. 15, 2011.

\* cited by examiner

*Primary Examiner* — Victoria P Shumate
(74) *Attorney, Agent, or Firm* — Stein McEwen, LLP (57) ABSTRACT

An insertion device for the introduction of a medical implement, the insertion device including a hollow body, a needle holder mounting portion, a needle holder, a needle adapted for a medical implement to be mounted therewith relative to the needle, biasing means to bias the needle and the needle holder into the hollow body, and a retaining mechanism adapted to at least temporarily retain the needle and the needle holder in a forward condition in which the needle extends forward of the hollow body against the biasing force of the biasing means. The retaining mechanism of the insertion device retains the needle and the needle holder in the forward condition until the medical implement is disassociated from the retaining mechanism and unless the retaining mechanism is operated independently to retain the needle holder and the needle in the forward condition.

21 Claims, 5 Drawing Sheets

MEDICAL IMPLEMENT INSERTION DEVICE

RELATED APPLICATION

This application claims priority from Australia provisional patent application No. 2010903644 filed 13 Aug. 2010.

TECHNICAL FIELD

The invention described herein generally relates to apparatus used for introduction of a medical implement used in intravenous therapy. In particular, the invention is directed to an insertion device with a retractable needle to assist in the insertion of medical implements such as catheters, cannulas and the like.

BACKGROUND

Intravenous ('IV') therapy is primarily used for the delivery of fluids into the vascular system of a patient. Medical implements associated with IV therapy, such as catheters and cannulas, can be inserted into a patient's blood vessel by using an insertion device. Insertion devices may comprise a needle on which a medical implement may be mounted and which guides the medical implement into a blood vessel, typically a vein, before the needle is withdrawn leaving the medical implement in the vein.

Standard insertion devices, after use, represent a health hazard in that they are a primary source of needlestick injuries and scratches. Such injuries heighten the risk of contamination and the transmission of diseases such as AIDS and hepatitis, which are present in or on the insertion device or in residual bodily fluids withdrawn with the device from a patient's vein. It is this residual fluid that is directly responsible for the transmission of diseases via needlestick injuries or scratches.

A number of safety insertion devices have been produced whereby the needle is safely retracted into the device. These types of safety devices can be generally divided into two types: 'active' insertion devices and 'passive' insertion devices. 'Active' insertion devices have a safety mechanism which is activated by the user after use of the insertion device whereas 'passive' insertion devices have safety mechanisms that do not require any action from the user.

Despite the benefits offered by the safety insertion devices over standard insertion devices a number of problems still exist. 'Active' insertion devices require users to be trained in the effective use of the device. Incorrect use of the device may result in the premature activation of the safety mechanism resulting in a device that then cannot be used, or worse, no activation after use which presents a needlestick injury risk.

'Passive' insertion devices can be unreliable in the automatic activation of the safety mechanism. For instance, the safety mechanism may activate prematurely or not at all. Due to the nature of their construction they contain many parts, which due to the large scale of manufacturing, are prone to failure.

Additionally, in general due to the extra parts involved in the manufacturing of safety insertion devices over standard insertion devices, both 'active' and 'passive' insertion devices tend to cost more.

When the safety mechanism of a safety insertion device is a retractable needle, the retraction mechanism tends to be spring loaded. The spring provides for an effective retraction force. A by product of the retraction force is that the retraction process can produce a retracting shock. Such shocks can cause residual fluid in the device to spray or squirt out of the rear of the device in what is known as 'splatter'. Such an effect is highly undesirable as it can cause cross contamination by direct contact with the residual body fluid or by breathing in splatter which is atomized in the air.

Finally, both 'active' and 'passive' safety insertion devices which are manufactured in a pre-assembled state with a medical implement are prone to becoming temporarily stuck to the medical implement. Such a situation, referred to as 'stiction', is undesirable especially once the safety insertion device has been used to insert the medical implement into a vein. The actions involved in disengaging the safety insertion device from the medical implement can lead to the premature activation of the safety mechanism in an 'active' safety insertion device or can damage the safety mechanism in both 'active' and 'passive' safety insertion devices to the extent that the safety mechanism is no longer functional. More importantly, such actions heighten the risk of a user obtaining a needlestick injury and the risk of a user being exposed to bodily fluids.

Thus, there is a need for a safety insertion device which is simple and reliable to use.

SUMMARY

In one form, the invention resides in an insertion device for the introduction of a medical implement, the insertion device including:

a hollow body with a forward opening and with a needle holder mounting portion;

a needle holder which extends at least partially into the hollow body through the forward opening;

a needle supported by the needle holder and adapted for a medical implement to be mounted therewith relative to the needle;

biasing means to bias the needle holder into a retracted condition in which the needle is received within the hollow body; and a retaining mechanism associated with the needle holder mounting portion and adapted to at least temporarily retain the needle holder in a forward condition in which the needle extends forward of the hollow body against the biasing force of the biasing means, wherein the medical implement includes a retention portion temporarily associated with the retaining mechanism of the insertion device to retain the needle holder in the forward condition until the retention portion is disassociated from the retaining mechanism and unless the retaining mechanism is operated independently of the retention portion to retain the needle holder in the forward condition.

In another form, the invention resides in an insertion device for the introduction of a medical implement, the insertion device including:

a hollow body with a forward opening and with a needle holder mounting portion;

a needle holder which extends at least partially into the hollow body through the forward opening;

a needle supported by the needle holder;

biasing means to bias the needle holder into a retracted condition in which the needle is received within the hollow body;

a retaining mechanism associated with the needle holder mounting portion and adapted to at least temporarily retain the needle holder in a forward condition in which the needle extends forward of the hollow body against the biasing force of the biasing means; and a medical implement with a retention portion mounted at least temporarily relative to the needle holder, wherein the retention portion is temporarily associated with the retaining mechanism of the insertion device to retain the needle holder in the forward condition until the retention portion is disassociated from the retaining mechanism and unless the retaining mechanism is operated independently of the retention portion to retain the needle holder in the forward condition.

In another form, the invention resides in a method of retracting a needle in an insertion device for the introduction of a medical implement, the insertion device comprising;

a hollow body with a forward opening and with a needle holder mounting portion;

a needle holder which extends at least partially into the hollow body through the forward opening;

a needle supported by the needle holder and adapted for a medical implement to mounted therewith relative the needle;

biasing means to bias the needle holder into a retracted condition in which the needle is received within the hollow body; and a retaining mechanism associated with the needle holder mounting portion and adapted to at least temporarily retain the needle holder in a forward condition in which the needle extends forward of the hollow body against the biasing force of the biasing means, a medical implement with a retaining portion mounted at least temporarily relative to the needle holder and at least temporarily associated with the retaining mechanism;

the method including the steps of:

disassociating the medical implement from the retaining mechanism;

releasing the retaining mechanism associated with the needle holder mounting portion which at least temporarily retains the needle holder in the forward condition; and     propelling the needle holder and the needle into the hollow body under the force of the biasing means.

The method may include a further sub-step of at least temporarily disassociating the medical implement from the retaining mechanism whilst contemporaneously maintaining manual pressure on the retaining mechanism to retain the needle holder in a forward condition in order to overcome stiction between the medical implement and the insertion device.

The medical implement can be any implement that can be inserted into a body cavity, duct, or vessel to allow drainage, injection of fluids, or access by surgical instruments. The medical implement may be a medical implement for intravenous therapy. Typically, the medical implement is a catheter or cannula including the protective cap, cover or the like associated with the catheter or cannula prior to use.

The hollow body of the insertion device may be of any suitable size and shape but will typically be cylindrical in design as is conventional, although if necessary, the body may have other shapes such as rectangular in cross-section, oval in cross-section and the like. The length of the hollow body may vary but it will be of a suitable length to completely encompass a needle (and needle holder) once in the retracted condition.

The hollow body of the insertion device will be hollow such that the needle holder and the needle can be contained therewithin. The hollow body will have a main inner longitudinal passageway or chamber which will typically be designed such that the needle holder and needle holder can pass along/into or at least partially along/into the main passageway or chamber. Access to the main passageway or chamber of the body will normally be provided by the forward opening.

According to a particularly preferred embodiment, the hollow body will have at least one grippable portion located on a side of the hollow body. Typically, the hollow body will have a pair of grippable portions, located on opposite sides of the hollow body to provide a user with points to hold the device. Preferably these grippable portions are positioned so as to allow pressure to be provided on the retaining mechanism to retain the needle holder in a forward condition against the biasing force of the biasing means.

A rear end of the hollow body may include an aperture which allows the stabilisation of the pressure inside the hollow body as a result of a change of volume when the needle holder and the needle are received within the hollow body in the retracted condition.

The hollow body may be made as a single piece or from two or more components such as a forward body component and a rear body component.

The hollow body can be made from any suitable material such as plastic, glass or even metal. Typically, the body will be made from plastics. Preferably, some parts of the hollow body or alternatively the whole hollow body will be made from a transparent material to enable visual confirmation of actions discussed below. Such transparent materials will typically be plastics such as polycarbonate or polypropylene, preferably high clarity polycarbonate.

The hollow body will have a needle holder mounting portion that is adapted to mount a needle holder and preferably receive and hold a needle holder. The needle holder mounting portion is typically located at a forward end of the hollow body and may be integrally formed with the hollow body. Alternatively, the needle holder mounting portion could be manufactured separately and then fixed to the hollow body at the forward end.

The needle holder mounting portion preferably includes a forward passageway through which the needle holder extends and is at least temporarily retained therein by the retaining mechanism. The forward passageway is preferably coaxially aligned with the main longitudinal passageway or chamber.

The forward passageway is preferably of reduced dimension compared to the main longitudinal passageway or chamber. The insertion device will also preferably have a portion of reduced outer dimension at or adjacent the forward end.

The needle holder mounting portion typically includes a collar portion with the forward passageway through the collar portion located coaxially with respect to the hollow body. The collar portion may be or include one or more projections extending axially forward of the hollow body.

According to a particularly preferred embodiment, such projections may be in the form of one or more resilient arms, or prongs, which lie against the needle holder when the needle holder is in the forward condition to hold, clamp, or otherwise restrain the needle holder in the forward condition. Typically two or more opposed resilient arms or prongs are provided. Typically the arms will have a rest position where sufficient distance is provided between the two or more opposed arms such that they will not interfere with the needle holder and the needle when the needle holder and the needle are retracted from the forward condition to the retracted condition. Preferably, however, the distance between the two or more opposed arms will be sufficient to stop a sealing member (discussed in detail below) as it is drawn rearwardly by the retraction of the needle. The two or more resilient arms are preferably forced toward one another such that the resilient arms are held under flexion against the sides of the needle holder.

The resilient arms typically taper from the collar portion to thinner ends to define an opening that diverges to a forward end of the hollow body thereby clearing any engagement with the needle holder.

Alternatively, there may be more than two resilient arms, such as three or four arms or prongs. The resilient arms may have a semi-circular profile shape. Any other arrangement is possible where a resilient grip is achieved on the needle holder.

According to an alternative embodiment, the needle holder mounting portion includes an annular collar with the forward passageway through the annular collar. The annular collar may include one or more projections extending laterally into the forward passageway of the hollow body. The walls of the annular collar are preferably resilient or to a small degree deformable, typically due to the preferred material of construction, in order to allow the annular collar to be deformed inwardly (preferably by engagement of the medical implement on the needle holder mounting portion or by imposition of force on the preferred grippable portions) in order to force engagement of the one or more projections with preferred corresponding detents on the needle holder and to be biased into an outward or normal condition in which the one or more projections are clear of the preferred detents allowing the needle holder to move relative to the hollow body.

Preferably, the needle holder mounting portion holds the needle holder through an inter-engagement arrangement between the needle holder mounting portion and the needle holder. This may be provided via a notch and corresponding projection arrangement provided in the needle holder and the needle holder mounting portion. Other types of male/female engagement profiles may be used depending upon the needle holder mounting portion used.

The needle holder mounting portion will preferably be formed of a material with resilient properties. Typically, the needle holder mounting portion will be formed of materials such as polycarbonate or polypropylene.

The needle holder which extends at least partially into the hollow body through the forward passageway comprises a body adapted to support a needle and be received within the hollow body. The body of the needle holder may be of any suitable size and shape but will typically be cylindrical in design as is conventional, although if necessary, the body may have other shapes such as rectangular in cross-section, oval in cross-section and the like. Typically the needle holder is an elongate hollow body with a barrel at the forward end into which the needle is fixed.

The needle holder will preferably have a flash chamber comprising a blood receiving internal chamber located somewhere from the middle to the rear of the needle holder's body with the rear of the flash chamber being closed off by a stopper. The body of the needle holder will typically be formed of a transparent material or have a transparent portion such that the flash chamber is externally visible or visible from outside the hollow body. The flash chamber receives a flash of blood as the needle enters a blood vessel thus alerting the user by way of a visual indicator to confirm entry into the blood vessel and whether the needle is in the correct position.

The positioning of the needle holder towards the forward end of the hollow body allows the user of the insertion device to comfortably operate the insertion device whilst at all times having a full visibility of the flash chamber, when the insertion device is used in a convention manner. This is particularly the case in the preferred embodiment where a pair of grippable portions are provided for correct use of the device and the flash chamber is offset from the grippable portions so as to remain relatively unobscured when the device is gripped using the grippable portions.

A portion of the needle holder, typically a rear portion preferably includes an outwardly or radially extending flange forming a shoulder relative to which a biasing means can be mounted in order to bias the needle holder into the retracted condition.

The body of the needle holder may have corresponding portion of the inter-engagement arrangement discussed earlier. A portion on the needle holder will preferably correspond with a portion of the inter-engagement arrangement on the needle holder mounting portion when in the forward condition and require the imposition of a force in order to maintain the engagement. Typically, the corresponding portion of the inter-engagement arrangement on the body of the needle holder comprises a notch to engage with a corresponding projection on the needle holder mounting portion. As indicated earlier, other types of male/female engagement profiles may be used depending upon the needle holder mounting portion used.

The needle holder can be formed of any suitable material such as glass, metal or plastic. Typically the needle holder is manufactured from plastics such as polycarbonate or polypropylene, preferably high clarity polycarbonate.

The stopper can be made of any material and may be integrally formed with the needle holder body. Typically the stopper is formed from an absorbent material such as paper or foam, preferably medical grade filter paper. The stopper is typically fitted to the needle holder during assembly of the insertion device.

The needle holder extends at least partially into the hollow body through the forward passageway, which is aligned with the main longitudinal passageway. The needle holder is adapted to be completely received within the hollow body when the needle holder is in the retracted condition. However, in the forward condition the needle holder is only partially extended into the hollow body such that the needle extends beyond the forward end of the hollow body and a medical implement can be relatively received therewith.

A needle is supported by the needle holder. The needle is positioned along the central axis of the needle holder and the insertion device. The needle is preferably a conventional hypodermic needle in that it is hollow and is in fluid communication with the flash chamber. Needles of different gauges may be used and may be indicated by colour coded needle holders, coloured according to the ISO standards (International organization for standardisations) to indicated different needle gauges.

The needle may at manufacture be inserted into the needle holder and affixed in place. Alternatively, the needle holder may be frictionally fitted to the needle holder, or manufactured with the needle in place. Preferably, the needle is secured in the needle holder with the use of an adhesive.

The needle supported by the needle holder is adapted for a medical implement to be mounted relative therewith the needle. As mentioned above the medical implement will be typically an implement to be used with the administration of IV therapy such as a cannula or catheter. The medical implement is mounted on the needle such that the needle extends at least partially but typically completely through the medical implement.

Medical implements with needles or tubes, for insertion into a patient, of varying diameter may be used. However the diameter of the needle or tube of the medical implement will sometimes be greater than the gauge of the needle of the insertion device such that the needle of the insertion device may extend within and through the needle or tube of the medical implement, such as in the case of a cannula and sometimes diameter of the needle or tube of the medical implement will be less than the gauge of the needle of the insertion device such that the medical implement may extend within and through the needle of the insertion device, such as in the case of a catheter tube.

Where the medical implement is a cannula, the medical implement is adapted to be mounted relative to the needle of the insertion device by sliding the medical implement over the needle and a hub of the medical implement (adapted to attach to other medical devices in use after location in a patient's body) over the distal portion of the resilient arms bringing the hub to rest adjacent to or abutting the annular collar of the insertion device. The hub of the medical implement once slid over the distal portion of the resilient arms will retain the resilient arms in a state of flexion against the sides of the needle holder thereby the maintaining the retaining mechanism in a state of engagement to effectively hold the needle holder in place.

The insertion device includes a biasing means to bias the needle holder and the needle into a retracted condition in which the needle holder and the needle are received within the hollow body. The biasing means can be of any size, shape or means that is suitably adapted to propel the needle holder and needle into and toward the rear end of the hollow body along the main passageway or chamber.

Typically the biasing means is a spring. The spring may comprise a helical spring that is located over and around the needle holder against the outwardly or radially extending flange of the needle holder such that when the needle holder is in the forward condition the spring is compressed between the inner edge of the collar portion and the outwardly or radially extending flange of the needle holder. Thus, the stored energy in the compressed spring provides the biasing force to propel the needle holder and the needle towards the rear end of the hollow body to the retracted condition.

The insertion device provides a retaining mechanism associated with the needle holder mounting portion and adapted to at least temporarily retain the needle holder in a forward condition in which the needle extends forwardly of the hollow body against the biasing force of the biasing means.

The retaining mechanism associated with the needle holder mounting portion can be any suitable force that is capable of forcing the needle holding mounting portion to engage with the needle holder. Typically, such force is a compressive force that maintains the resilient arms, under flexion, against the needle holder such that the needle holder is held by the needle holder-mounting portion in the forward condition. Alternatively, the force may be a compressive force applied to the annular collar that forces the annular collar to reduce in diameter and engage with and hold the needle holder in a forward condition.

Preferably, compressive force is applied to the needle holder mounting portion at least initially by the hub of a medical implement when it is fitted proximal the annular collar over the distal portion of the resilient arms thereby holding them against the needle holder.

Compressive force may also be applied to the needle holding mounting portion via the grippable portions on the external surface of the hollow body. Typically, the compressive force applied by the user's grip is applied through grippable portions to the resilient arms thereby compressing the arms against the needle holder and retaining the needle holder in a forward position against the biasing force of the biasing means.

The grippable portions of the hollow body are formed of a resilient material capable of being squeezed and transferring a compressive force to the needle holder mounting portion underneath. Typically the grippable portions are formed of resilient plastics, preferably polycarbonate or polypropylene.

Optionally, the inter-engagement arrangement described previously may be used in addition to the compressive force applied to the needle holding mounting portion to force the resilient arms against the needle holder to retain the needle holder in a forward condition. Compressive force applied by to the needle holder mounting portion via the mounted medical implement and/or pressure applied to the grippable portions forces the male/female inter-engagement portions located on the needle holder mounting portion and the needle holder together to thereby further secure the needle holder in a forward condition.

In use, the medical implement, when mounted on the needle, either includes a retention portion temporarily associated with the retaining mechanism of the insertion device to retain the needle holder and the needle in a forward condition until the retention portion is disassociated from the retaining mechanism and unless the retaining mechanism is operated independently of the retention portion to retain the needle holder in a forward condition or alternatively, a separate retention portion may be provided to achieve the same effect.

The retention portion of the medical implement can be any feature of the medical implement or associated with the medical implement or insertion device that is able to force the needle holder mounting portion to remain engaged with the needle holder. Typically such a feature will maintain the resilient arms, under flexion, against the needle holder. Preferably, the retention portion will be the hub of a cannula which when mounted on the needle rests proximal to the annular collar of the insertion device and over the distal portion of the resilient arms. If a catheter is the medical implement, the retention portion may be or include a ring or similar which is received over the resilient arms until removed.

Once the medical implement is disengaged from the insertion device such that the retention portion of the medical implement is disassociated from the retaining mechanism or the retention portion is otherwise removed, the force is removed from the needle holder mounting portion and the needle holder mounting portion and the needle are propelled by the biasing force of the biasing means into the hollow body.

The needle holder and the needle may be temporarily retained in the forward condition once the medical implement has been disengaged from the retention portion of the medical implement by independent operation of the retaining mechanism. The independent operation of the retaining mechanism can be any force capable of retaining the needle holder mounting portion in an engaged stated with the needle holder. Typically the force is a compressive force applied to the needle holder mounting portion to thereby retain the needle holder mounting portion in state of flexion against the needle holder. Preferably, the force is a compressive force applied to the grippable portions of the insertion device by a user when holding the insertion device in a normal manner, the compressive force being applied through the grippable portions to the two resilient arms which are located underneath the grippable portions. The compressive force keeps the resilient arms in a state of flexion against the sides of the needle holder and thereby retaining the needle holder in a forward condition.

The insertion device may also comprise at least one sealing member adapted to seal the needle holder and the needle in the hollow body when the needle holder is in a retracted condition. A sealing member may be located within the hollow body toward the forward end of the hollow body and is drawn rearwardly as the needle holder and the needle are propelled into the hollow body by the biasing force.

Preferably, the sealing member is located at the distal forward end of the insertion device between the distal ends of the resilient arms in an annular arrangement around the needle such that when the needle holder and the needle retract the needle is drawn through the sealing member. The sealing member is drawn rearwardly with the needle and the needle holder by frictional force. The sealing member is preferably stopped in its rearward movement by the inward projection portion provided on the needle holder mounting portion as part of the inter-engagement arrangement.

The sealing member may be formed of an absorbent material adapted to contain any residual blood or bodily fluids that remain on or in the needle. Preferably the sealing member is formed of an absorbent foam.

The hollow body may further comprise a damper located a short distance from the rear end of the hollow body. The damper may be displaced from its position by the needle holder when the needle holder is propelled rearwardly into the hollow body under the biasing force. Typically, the stopper end of the needle holder will come into contact with the damper. The damper will preferably be displaced from its initial location to a final position at the end of the hollow body. In this function the damper acts as a shock absorber.

Preferably the end of the hollow body is transparent such that the damper, once displaced, is visible thus quickly alerting a user to the fact that the needle holder is in the retracted condition. The damper in its initial location will be, preferably, hidden underneath a band around the hollow body. The damper once displaced from behind the band will preferably indicate the retraction of the needle holder.

The band may be colour coded according to the ISO standards to indicate various needle gauges. The damper may also be colour coded to allow for easy visualisation and identification that the needle holder has retracted. The damper can be made of any type of material suitable for shock absorbing and/or sealing. Preferably the damper will be formed of a material such as foam.

Any of the features of the invention disclosed herein may be claimed in any combination with any of the other features.

BRIEF DESCRIPTION OF THE DRAWINGS

In order that the invention may be more readily understood and put into practice, one or more preferred embodiments thereof will now be described, by way of example only, with reference to the accompanying drawings, in which.

DETAILED DESCRIPTION

It will be appreciated that the drawings have been provided for the purpose of illustrating preferred embodiments of the present invention. It will be understood that the present invention should not be considered to be limited solely to the features shown in the drawings.

One embodiment of the present invention is illustrated in the drawings that shows an insertion device 10 broadly having a hollow body 12 with a forward opening 14, a needle holder mounting portion 16, a needle holder 18 supporting a needle 20 that is adapted for a medical implement such as a cannula 22 to be mounted therewith relative to the needle 20. Biasing means in the form of a spring 24 bias the needle holder 18 and the needle 20 into a retracted condition in which the needle holder 18 and the needle 20 are received within the hollow body 12. A retaining mechanism 26 associated with the needle holder mounting portion 16 temporarily retain the needle holder 18 and the needle 20 in a forward condition against the biasing force of the spring 24. The cannula 22 includes a retention portion 28 that is temporarily associated with the retaining mechanism 26, whilst the cannula 22 is mounted on the needle 20, to thereby retain the needle holder 18 and the needle 20 in a forward condition. Once the retention portion 28 of the cannula 22 is disassociated from the retaining mechanism 26 the needle holder 18 and the needle 20 will be retracted into the hollow body 12 unless the retaining mechanism 26 is operated independently of the retention portion 28 to retain the needle holder 18 and the needle 20 in a forward condition.

The hollow body 12 is a long cylindrical component having an internal catchment chamber 30 which can be made as a single piece or two or more components as illustrated in the figures, which show the hollow body 12 formed from a forward body part 12a and a rear body part 12b. Grippable portions 32 are located on opposed sides of the hollow body 12 to provide the user with points to hold the insertion device 10. The end of the hollow body 12 includes an aperture 34 which allows the stabilisation of pressure in the catchment chamber 30 inside the hollow body 12 as a result of a change of volume of the catchment chamber 30 during retraction of the needle holder 18 and the needle 20.

The needle holder mounting portion 16 comprises a collar portion 36 defining the central opening 14 with projections in the form of two resilient arms 38 extending axially forward from the collar portion 36. An inter-engagement arrangement 40 in the form of a notch 42 on the needle holder 18 and corresponding projection 44 on the needle holder mounting portion 18 further serve to retain the needle holder 18 and the needle 20 in a forward condition when the resilient arms 38 are held, under flexion, against the sides of the needle holder 18.

The body 48 of the needle holder 18 is hollow and has a flash back chamber 46 located at the middle to rear of the needle holder's body 48. The rear of the needle holder is closed off by a stopper 50. The rear of the body 48 of the needle holder 18 has an outer flange 52 around which the spring 24 can be fitted.

The needle 20 supported by the needle holder 18 is a convention needle that is hollow and in fluid communication with the flash back chamber 46.

The retention portion 28 of the cannula 22 is adapted to be mounted on the needle 20 by sliding a cannula needle 54 over the needle 20 and sliding the retention portion 28 over the distal portion of the arms 38 and thereby compressing the arms 38 against the needle holder 18 and bringing the retention portion 28 to rest proximal to the collar portion 36.

The retaining mechanism 26 is located at a forward end of the hollow body 12 and in the embodiment illustrated the retaining mechanism 26 is integrally formed with the hollow body 12. In an alternate embodiment the retaining mechanism could be manufactured separately and fixed inside the body at the forward end. The retaining mechanism 26 is associated with the needle holder mounting portion 16 and is activated by any suitable compressive force that is capable of forcing the needle holder mounting portion 16 to engage with the needle holder 18. One such force is generated by the retention portion 28 of the cannula 22 when mounted on the needle 20 and holding the resilient arms 38 against the needle holder 18. An alternative force can be applied by the user of the insertion device 10 to activate the retaining mechanism 26 through the user's grip. Compressive force from the user's grip can be applied to both or one of the resilient arms 38 via the corresponding grippable portions 32. Each grippable portion 32 is located directly above one of the resilient arms 38.

The embodiment of the insertion device 10 illustrated in the figures further comprises a sealing member 56, which resides between the distal ends of the resilient arms 38. The sealing member 56 serves to absorb any residual bodily fluids or blood on the needle 20 when the needle 20 and the needle holder 18 are retracted into the hollow body 12. Furthermore, the sealing member 56 serves to seal the forward opening 14 of the device 10 to retain any residual bodily fluids, blood or the like which are retracted also into the hollow body thereby reducing the risk of splatter.

A damper 58 is located near the end of the hollow body 12. The damper 58 absorbs the shock of the retraction of the needle holder 18 and the needle 20. Additionally, the damper 58 is displaceable from its position a short distance from the end of the hollow body 12 where it is hidden behind a band 60 to a position at the end of the hollow body 12. Displacement of the damper 58 from behind the band 60 to a position at the end of the body 12 where it is visible to the user alerts the user that the needle 20 has successfully retracted into the hollow body 12.

Figure 1:
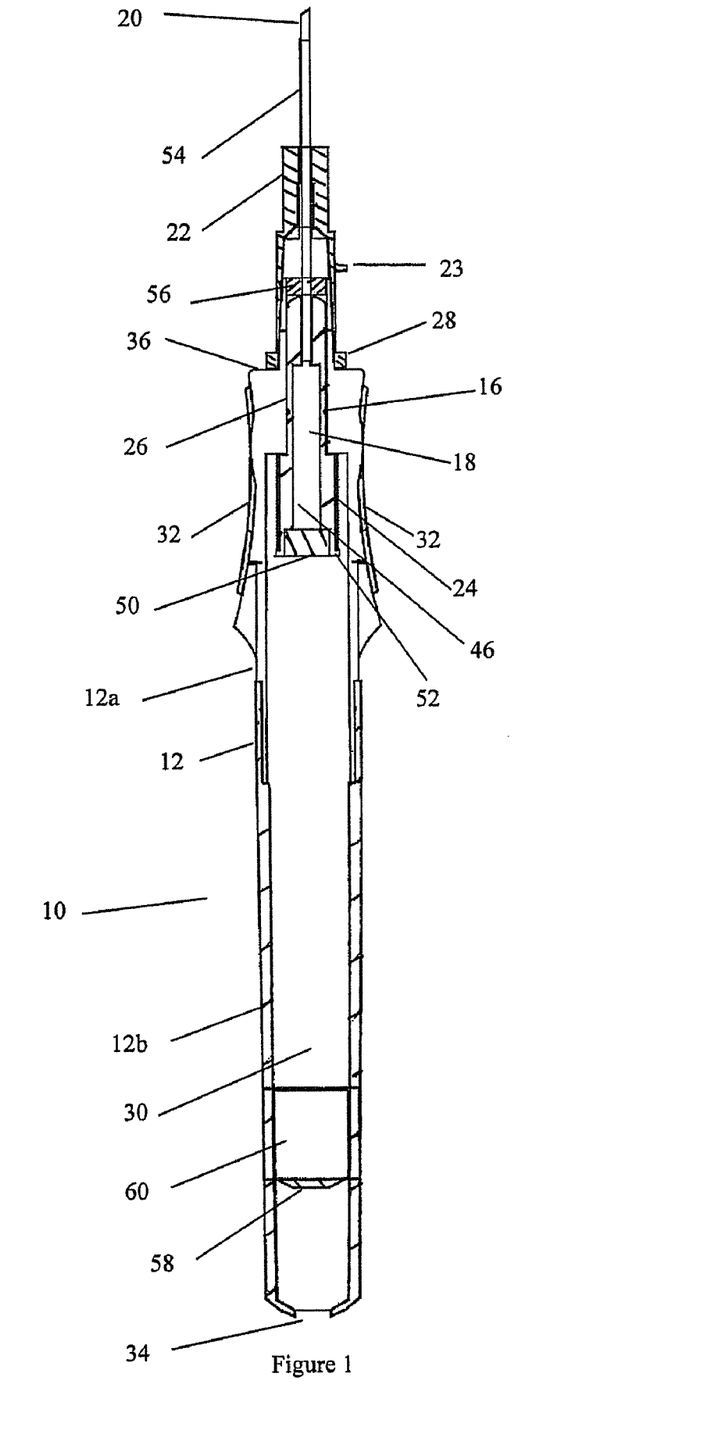
FIG. 1 is a side sectional view of an insertion device with a mounted cannular, the insertion device being in an operative condition and in accordance with an embodiment of the present invention.

FIG. 1 shows the insertion device 10 in a state ready to use. The user prepares the site of insertion on a patient and places the needle 20, which extends past the end of the cannula needle 54, against the patient's skin. The needle 20 has a bevelled end 21 facing upward. The user then inserts the needle tip into the skin of the patient and pushes both the needle and the cannula needle 54 into the vein in accordance with the correct procedure. Flash back will occur after the needle is in the vein and may occur before the cannula needle is fully within the vein. At this point the insertion device is still assembled as shown in FIG. 1 with all components fully engaged. The needle 20 is then disengaged from the cannula 22. This may be achieved by applying pressure to a push-off tab 23 located on the side of the cannula 22.

Figure 2:
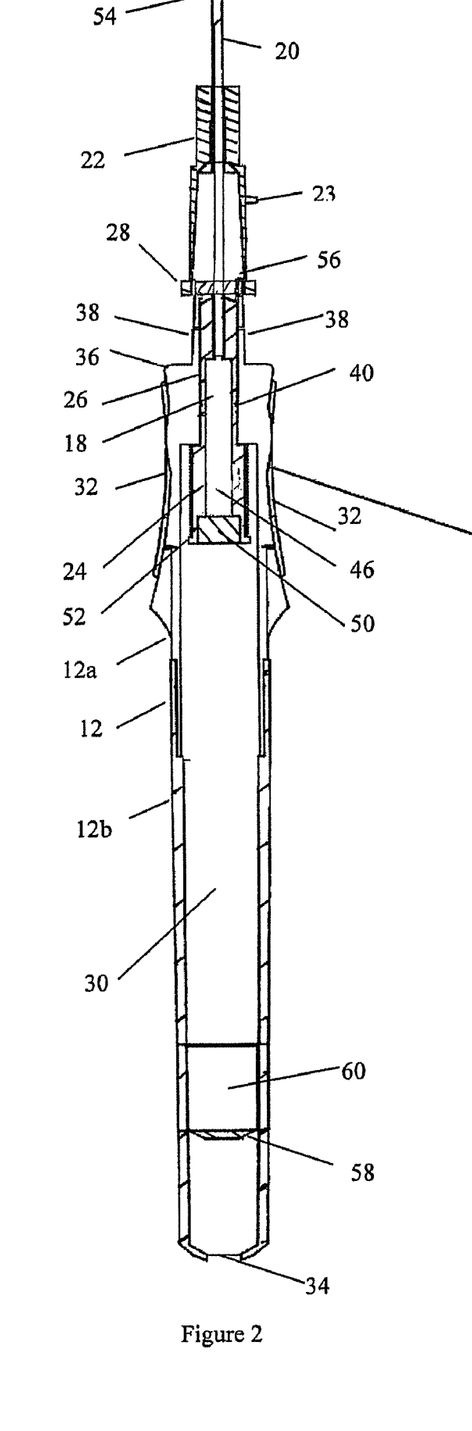
FIG. 2 is a side sectional view showing the device of FIG. 1 withdrawing from the cannula with pressure applied to the grippable portions.

FIG. 2 shows the stage at which the needle 20 is disengaging from the cannula 22 with the retention portion 28 separating from the collar portion 36. As the retention portion 28 slides off the resilient arms 38, the compressing forces applied by the retention portion 28 to the resilient arms 38 will be removed. However, the resilient arms 38 are maintained in a position of flexion against the needle holder 18 by pressure applied by a user to at least one of the grippable portions 32. In this way the user controls when the needle retracts. Once the user releases the insertion device 10 thereby removing any pressure applied to at least one of the grippable portions 32 all compressing forces are removed and retraction of the needle holder 18 and the needle 20 under the biasing force of the spring 24 is initiated.

Figure 3:
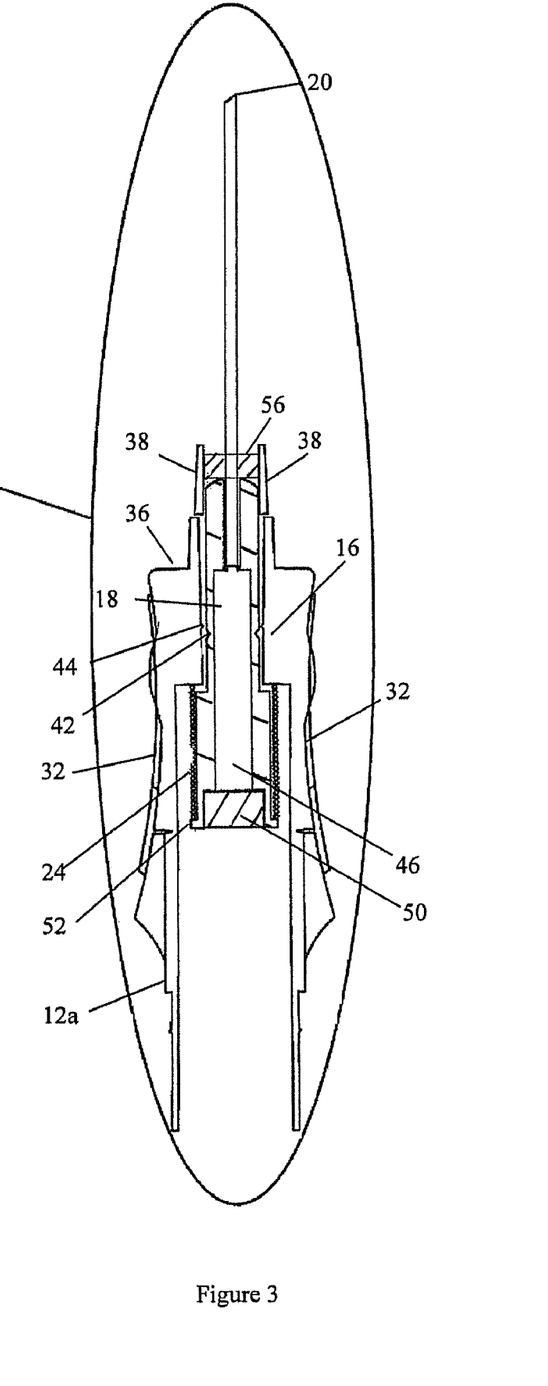
FIG. 3 is a magnified side sectional view showing the forward end of the device of FIG. 1 when the retraction process has just initiated.

FIG. 3 shows the stage at which the cannula 22 has been completely disengaged from the insertion device 10 and the user has removed any pressure applied to any one of the grippable portions 32 thereby removing all compressing forces maintaining the resilient arms 38 in positions of flexion. The resilient arms 38 now being free begin to spread and return to their rest positions releasing their engagement with the needle holder 18. As soon as the needle holder mounting portion 16 no longer retains the needle holder 18, the stored energy in the compressed spring 24 starts to release and propel the needle holder 18 and therefore the needle 20 rearwardly.

Figure 4:
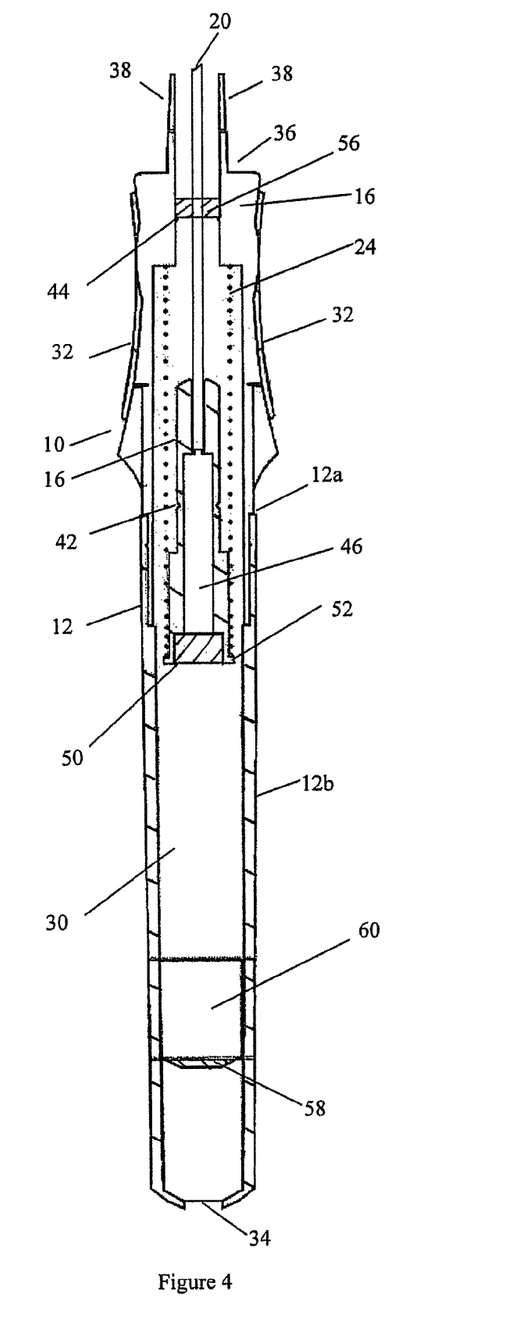
FIG. 4 is a side sectional view showing the device of FIG. 1 with the needle and the needle holder partially retracted.

FIG. 4 shows the needle holder 18 and needle 20 beginning to retract into the hollow body 12. The needle 20 as it is being retracted is drawn through a sealing member 56 and thereby draws the sealing member 56 rearwardly until it engages with and is retained by the inwardly facing projections 44 on the needle holder mounting portion 16.

Figure 5:
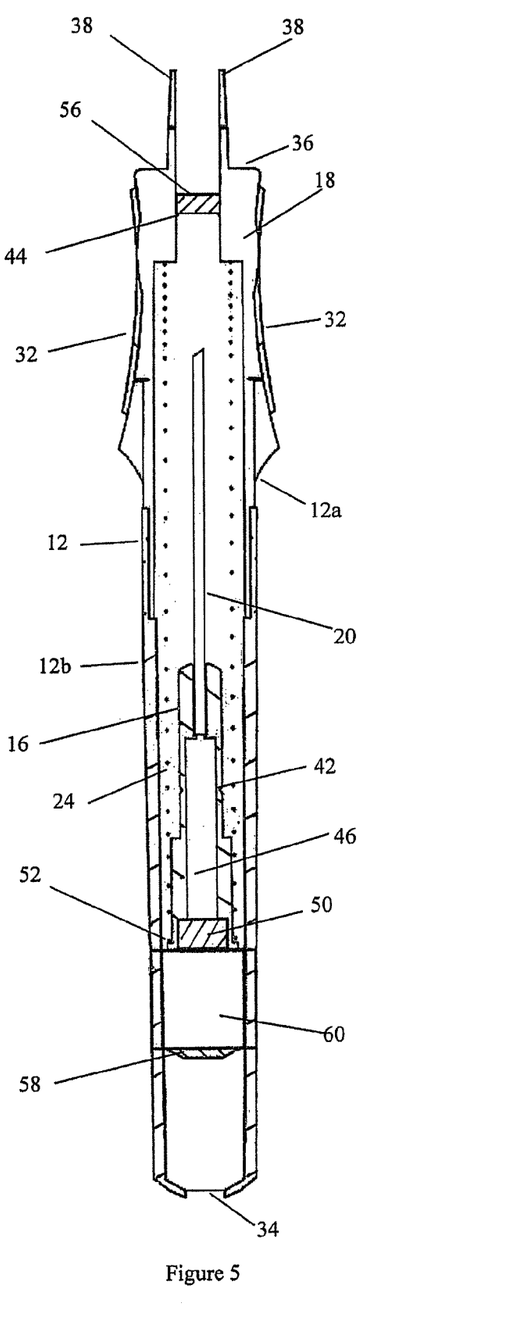
FIG. 5 is a side sectional view showing the device of FIG. 1 showing almost complete retraction of the needle holder and the needle.

FIG. 5 shows the stage at which the needle holder 18 and needle 20 are almost to the full point of retraction with the needle 20 fully retracted into the catchment chamber 30. At this stage the needle 20 has been fully drawn through the sealing member 56. The sealing member 56 now forms a barrier to keep any blood or bodily fluid that is retracted by the needle 20 and/or needle holder 18 back in to the hollow body 12, in the hollow body 12 thereby preventing cross contamination via leakage of the insertion device 10. At this point the flash back chamber 46 will contain blood or bodily fluids. The stopper 50 of the needle holder 18 toward the rear of the catchment chamber will come into contact with a damper 58. The damper 54 absorbs the shock of the retraction.

Figure 6:
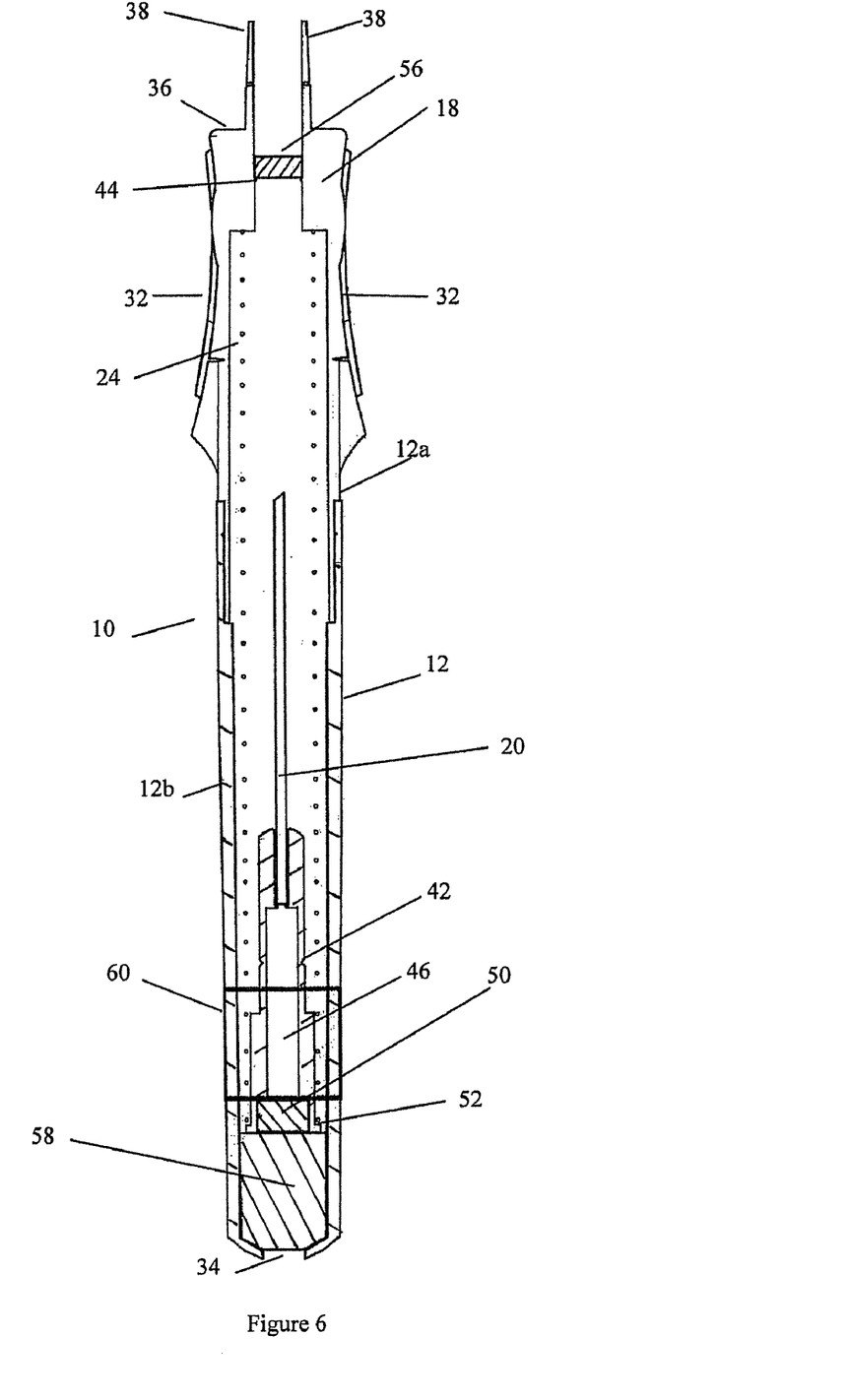
FIG. 6 is a side sectional view of showing the device of FIG. 1 showing complete retraction of the needle holder and the needle.

FIG. 6 shows the stage at which the needle holder 18 and the needle 20 have been fully retracted into the hollow body 12 of the insertion device 10. Now the damper 54 has been displaced from its position a short distance from the end of the hollow body 12 behind the band 60 to its final position at the end of the hollow body 12.

Figure 7:
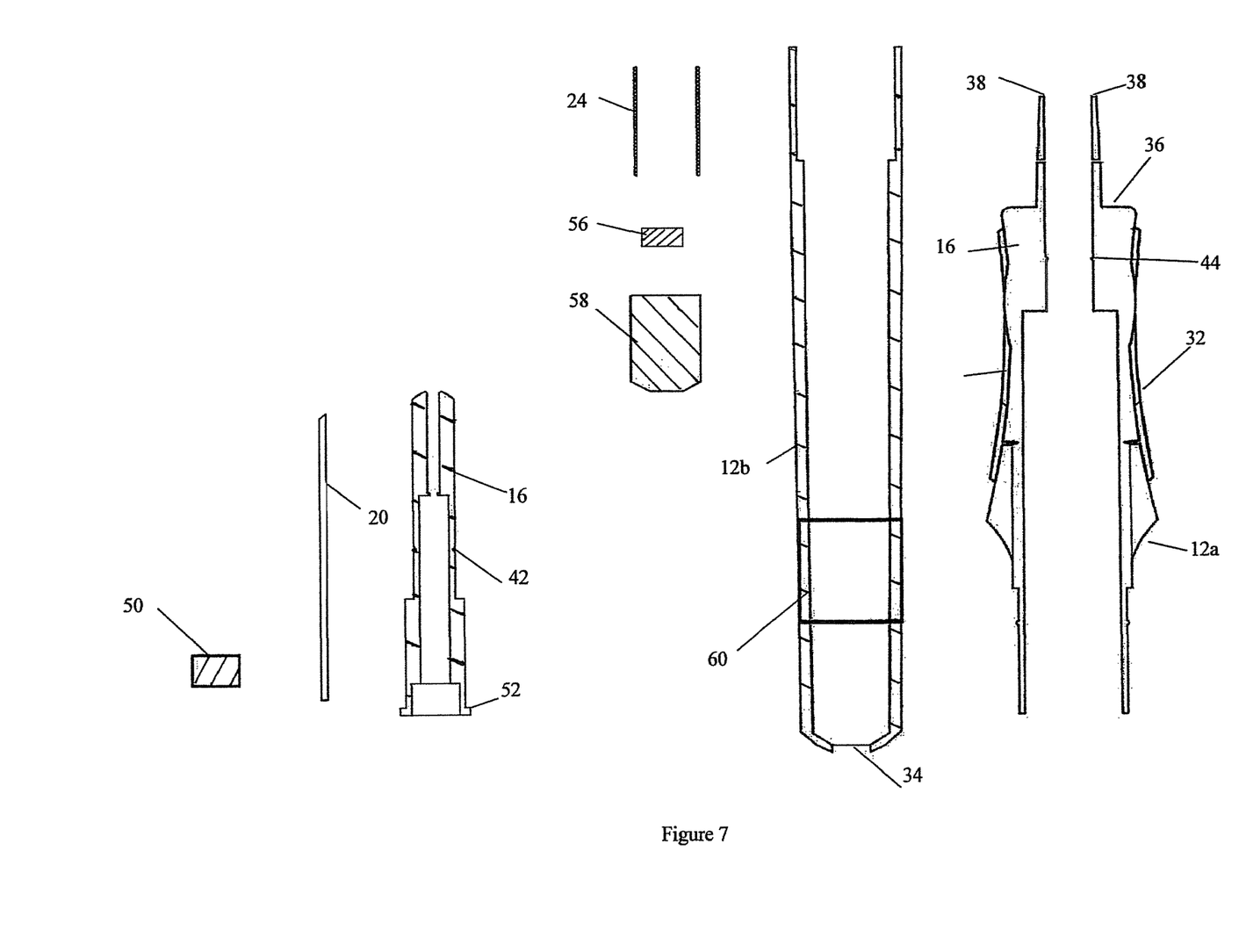
FIG. 7 is an exploded view of the needle holder, the needle holder mounting portion and the forward and rear parts of the body of the device of FIG. 1.

FIG. 7 shows separately the parts of the needle holder 18, the needle holder mounting portion 16 which forms the forward part of the hollow body 12a, and the rear part of the hollow body 12b.

The foregoing embodiments are illustrative only of the principles of the invention, and various modifications and changes will readily occur to those skilled in the art. The invention is capable of being practiced and carried out in various ways and in other embodiments. It is also to be understood that the terminology employed herein is for the purpose of description and should not be regarded as limiting.

In the present specification and claims, the word 'comprising' and its derivatives including 'comprises' and 'comprise' include each of the stated integers but does not exclude the inclusion of one or more further integers.

Reference throughout this specification to 'one embodiment' or 'an embodiment' means that a particular feature, structure, or characteristic described in connection with the embodiment is included in at least one embodiment of the present invention. Thus, the appearance of the phrases 'in one embodiment' or 'in an embodiment' in various places throughout this specification are not necessarily all referring to the same embodiment. Furthermore, the particular features, structures, or characteristics may be combined in any suitable manner in one or more combinations.

In compliance with the statute, the invention has been described in language more or less specific to structural or methodical features. It is to be understood that the invention is not limited to specific features shown or described since the means herein described comprises preferred forms of putting the invention into effect. The invention is, therefore, claimed in any of its forms or modifications within the proper scope of the appended claims appropriately interpreted by those skilled in the art.

The invention claimed is:

1. An insertion device for the introduction of a medical implement, the insertion device including:
   a hollow body with a forward opening and with a needle holder mounting portion;
   a needle holder which extends at least partially into the hollow body through the forward opening;
   a needle supported by the needle holder and adapted for a medical implement to be mounted therewith relative to the needle;
   biasing means to bias the needle holder into a retracted condition in which the needle is received within the hollow body; and
   a retaining mechanism associated with the needle holder mounting portion and adapted to at least temporarily retain the needle holder in a forward condition in which the needle extends forward of the hollow body against the biasing force of the biasing means,
   wherein the medical implement includes a retention portion temporarily associated with the retaining mechanism,
   wherein the retention portion temporarily associated with the retaining mechanism retains the needle holder in the forward condition until the retention portion is disassociated from the retaining mechanism and the retaining mechanism is operated independently of the retention portion to retain the needle holder in the forward condition, and
   wherein the retaining mechanism is operated independently through the application of a compressive force to at least two portions located on the external surface of the hollow body adjacent the retaining mechanism.

2. The insertion device of claim 1, wherein the needle holder mounting portion is located towards a forward end of the hollow body defining the forward opening and a forward passageway through which the needle holder is at least temporarily retained in the forward condition by the retaining mechanism.

3. The insertion device of claim 2, wherein the needle holder mounting portion includes a collar portion through which the forward passageway extends in coaxial alignment with respect to the hollow body.

4. The insertion device of claim 1, wherein the needle holder mounting portion includes one or more resilient prongs associated with the retaining mechanism and extending axially forward of the hollow body and adapted to lie against the needle holder to at least temporarily retain the needle holder in the forward condition.

5. The insertion device of claim 4, wherein the needle holder mounting portion includes at least two opposed resilient prongs.

6. The insertion device of claim 5, wherein the at least two opposed resilient prongs have a rest position in which sufficient distance is provided between the at least two opposed resilient prongs such that the at least two opposed resilient prongs will not interfere with the needle holder and the needle when the needle holder and the needle are retracted from the forward condition to the retracted condition.

7. The insertion device of claim 6, wherein the retention portion of a medical implement associated with the insertion device retains the needle holder in the forward condition by retaining the at least two opposed resilient prongs under flexion against the needle holder.

8. The insertion device of claim 6, wherein the retaining mechanism of the insertion device is operated independently once a medical implement is dissociated from the insertion device to at least temporarily retain the needle holder in the forward condition by retaining the at least two opposed resilient prongs under flexion against the needle holder.

9. The insertion device of claim 8, wherein the at least two portions are resilient grippable portions and the compressive force applied to the resilient grippable portions when the retaining mechanism is independently operated is transferred to the at least two opposed resilient prongs of the retaining mechanism.

10. The insertion device of claim 9, wherein the compressive force applied to the grippable portions is substantially the same as the force applied by a user when holding the insertion device in a normal manner.

11. The insertion device of claim 1, wherein the needle holder mounting portion and the needle holder include an inter-engagement arrangement.

12. The insertion device of claim 11, wherein the inter-engagement arrangement comprises a notch and corresponding projection arrangement provided on an outer wall of the needle holder and the inner wall of the needle holder mounting portion, respectively.

13. The insertion device of claim 1, wherein the biasing means is a helical spring located over and around the needle holder against an outwardly extending flange located on a rear portion of the needle holder and an inner forward edge of the needle holder mounting portion.

14. The insertion device of claim 1 further comprising a sealing member located at the distal end of the insertion device and adapted to substantially seal the needle holder and the needle in the hollow body when the needle holder and the needle are in the retracted condition.

15. The insertion device of claim 1, wherein the needle holder includes a flash back chamber located towards the rear of the needle holder and adapted to be visible by a user when the insertion device is used in a conventional manner.

16. The insertion device of claim 15, wherein the exterior surface of the hollow body adjacent the flash back chamber is transparent to enable visualisation of the flash back chamber.

17. The insertion device of claim 1, wherein the hollow body includes a damper located towards the rear end of the hollow body, wherein the damper is adapted to be displaced by the needle holder when the needle holder and the needle are propelled rearwardly under the biasing force of the biasing member.

18. An insertion device for the introduction of a medical implement, the insertion device including:
   a hollow body with a forward opening and with a needle holder mounting portion;
   a needle holder which extends at least partially into the hollow body through the forward opening;
   a needle supported by the needle holder;
   biasing means to bias the needle holder into a retracted condition in which the needle is received within the hollow body;
   a retaining mechanism associated with the needle holder mounting portion and adapted to at least temporarily retain the needle holder in a forward condition in which the needle extends forward of the hollow body against the biasing force of the biasing means; and a medical implement with a retention portion mounted at least temporarily relative to the needle holder, wherein the retention portion is temporarily associated with the retaining mechanism of the insertion device to retain the needle holder in the forward condition until the retention portion is disassociated from the retaining mechanism and the retaining mechanism is operated independently of the retention portion to retain the needle holder in the forward condition, and wherein the retaining mechanism is operated independently through the application of a compressive force to at least two portions located on the external surface of the hollow body adjacent the retaining mechanism.

19. A method of retracting a needle in an insertion device for the introduction of a medical implement as defined in claim 18, the method including the steps of:

disassociating the medical implement from the retaining mechanism;

releasing the retaining mechanism associated with the needle holder mounting portion which at least temporarily retains the needle holder in a forward condition; and propelling the needle holder and the needle into the hollow body under the force of the biasing means.

20. The method of claim 19 including a further sub-step of at least temporarily dissociating the medical implement whilst contemporaneously maintaining the manual pressure on the retaining mechanism to retain the needle holder in the forward condition in order to overcome stiction between the medical implement and the insertion device.

21. An insertion device for the introduction of a medical implement, the insertion device including:

a hollow body with a forward opening and with a needle holder mounting portion including at least two opposed resilient prongs;

a needle holder which extends at least partially into the hollow body through the forward opening;

a needle supported by the needle holder and adapted for a medical implement to be mounted therewith relative to the needle;

biasing means to bias the needle holder into a retracted condition in which the needle is received within the hollow body; and a retaining mechanism associated with the needle holder mounting portion and adapted to at least temporarily retain the needle holder in a forward condition in which the needle extends forward of the hollow body against the biasing force of the biasing means, wherein the medical implement includes a retention portion temporarily associated with the retaining mechanism, wherein the retention portion temporarily associated with the retaining mechanism retains the needle holder in the forward condition until the retention portion is disassociated from the retaining mechanism and the retaining mechanism is operated independently of the retention portion to retain the needle holder in the forward condition, and wherein the retaining mechanism is operated independently through the application of a compressive force to at least two resilient grippable portions located on the external surface of the hollow body adjacent the at least two opposed resilient prongs such that the compressive force applied to the resilient grippable portions is transferred to the at least two opposed resilient prongs.

* * * * *